(12) United States Patent
Donato

(10) Patent No.: US 6,932,783 B1
(45) Date of Patent: Aug. 23, 2005

(54) PASSIVE HIP REDUCER

(76) Inventor: James C. Donato, 5114 Ashton Rd., Sarasota, FL (US) 34233

( * ) Notice: Subject to any disclaimer, the term of this patent is extended or adjusted under 35 U.S.C. 154(b) by 0 days.

(21) Appl. No.: 10/978,637

(22) Filed: Oct. 30, 2004

(51) Int. Cl.[7] .............................................. A61F 5/00
(52) U.S. Cl. ............................ 602/36; 602/32; 602/67; 128/845; 128/846; 128/882; 5/624; 5/648
(58) Field of Search ...................... 602/32–40, 60–63, 602/67, 19, 5; 128/845, 846, 870, 876, 882, 128/898; 5/600, 618, 619, 621, 623, 624, 5/630, 648

(56) References Cited

U.S. PATENT DOCUMENTS

| | | | |
|---|---|---|---|
| 1,213,373 A | | 1/1917 | Hollowell |
| 2,044,299 A | * | 6/1936 | Hawley ........................ 602/38 |
| 4,489,713 A | | 12/1984 | Latenser |
| 4,602,618 A | | 7/1986 | Berze |
| 4,624,245 A | * | 11/1986 | Mullin et al. .................. 602/38 |
| 4,664,099 A | | 5/1987 | Pearl, Jr. |
| 4,879,994 A | * | 11/1989 | Watanabe ..................... 602/36 |
| 5,303,716 A | | 4/1994 | Mason et al. |
| 5,312,323 A | | 5/1994 | McAninch |
| 5,509,894 A | | 4/1996 | Mason et al. |
| 5,522,792 A | * | 6/1996 | Bassett et al. ................. 602/19 |
| 5,608,934 A | * | 3/1997 | Torrie et al. .................... 5/624 |
| 6,003,176 A | * | 12/1999 | Wasley et al. .................. 5/624 |
| 6,298,507 B1 | * | 10/2001 | Clyburn ......................... 5/623 |
| 6,311,349 B1 | * | 11/2001 | Kazakia et al. ................. 5/624 |
| 6,622,324 B2 | * | 9/2003 | VanSteenburg et al. ........ 5/621 |
| 2003/0154550 A1 | | 8/2003 | Murphy et al. |

* cited by examiner

Primary Examiner—Fadi H. Dahbour
(74) Attorney, Agent, or Firm—Larson & Larson, PA; Herbert W. Larson

(57) ABSTRACT

A patient with a dislocated hip lies on a planar pad having side rails along which slides a frame having upright members on each side of the pad and a horizontal member connecting the top of the upright members. A first winch mounted on an upright member controls cables connected to a mid-portion of a leg sleeve on the patient to lift the patient's leg. A second winch mounted on the same upright member controls cables connected to a top portion of the leg sleeve to pull the patient's hip outwardly to a normal position in the hip socket.

16 Claims, 5 Drawing Sheets

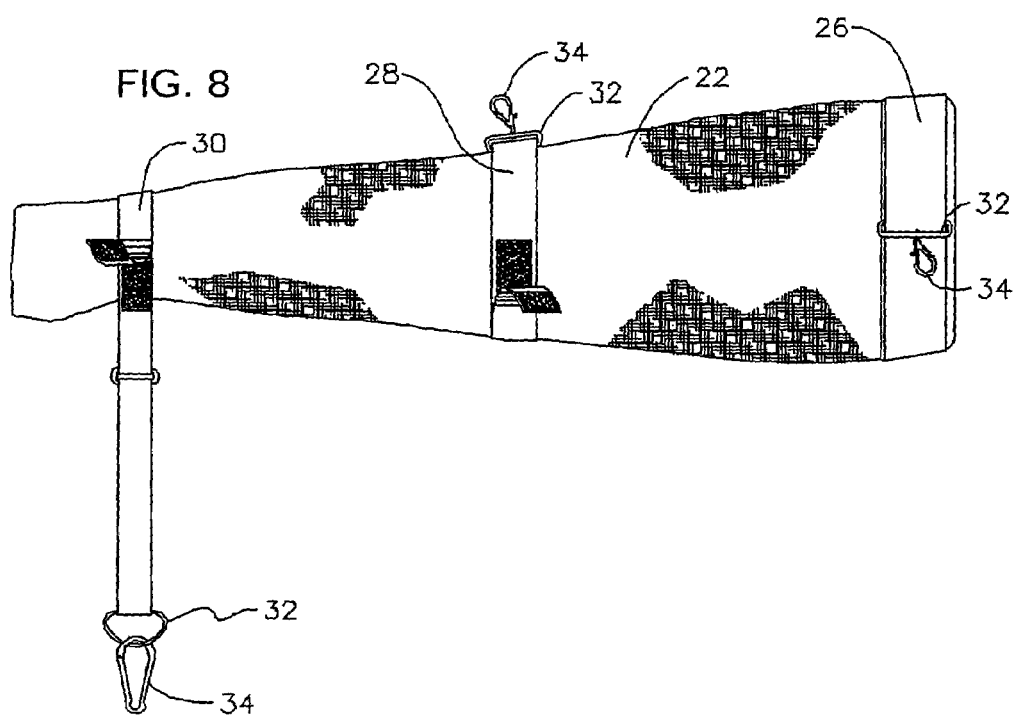

PASSIVE HIP REDUCER

BACKGROUND OF THE INVENTION

1. Field of the Invention

The present invention relates to a mechanical device for returning a patient's dislocated hip to its normal position. More specifically, it refers to a system and method of employing a disposable leg sleeve together with a winch and pulley system to place a patient in an optimum position for hip reduction.

2. Description of the Prior Art

It is customary for a physician and physician's assistant with the assistance of a nurse to physically and actively manipulate a patient's dislocated hip to return it to its normal position in the patient's body. Such manipulation is painful to the patient, requires anesthesia and takes substantial time and physical effort on the part of both the physician and physician's assistant. It is known to employ passive exercise to a hip-joint following surgery as seen in U.S. Pat. No. 4,602,618. This passive exercise involves a power drive imparting compound swivel movement to a leg cradle and patient's leg about an orthogonal axis centered at the socket of the hip-joint. Although active manipulation usually results in returning a dislocated hip to a normal position in the socket of the hip-joint such a method requires time and extended effort on the part of a skilled physician and physician's assistant. The passive exercise set forth in the U.S. Pat. No. 4,602,618 is not designed to reduce the patient's hip, but merely exercise the hip. A need exists for a system of passively reducing a dislocated hip.

SUMMARY OF THE INVENTION

The present invention provides a solution to the prior art need by providing a passive system for reducing a patient's dislocated hip. The patient is supported on a padded board having side rails. A frame is movable along the rails to position a pulley system approximately above a patient's waist. A first winch attached to a frame upright side member controls a cable passing through pulleys attached to a horizontal frame member. The leg of the patient on the side of the dislocated hip is covered with a sleeve. A pair of pelvis straps attached to the padded board are tightly attached around the waist of the patient. The first winch controls cables attached to a mid-portion of the sleeve to lift the patient's leg. A second winch attached to the same upright frame side member controls a cable attached to an upper portion of the sleeve to pull the patient's hip towards the upright frame member. As the two winches are turned sufficient torque is exerted on the patient's hip to return it to a normal body position.

BRIEF DESCRIPTION OF THE DRAWINGS

This invention can be best understood by those having ordinary skill in the art by reference to the following detailed description, when considered in conjunction with the accompanying drawings in which:

FIG. 8 is a side elevational view of the leg sleeve employed with the passive hip reducer apparatus.

DETAILED DESCRIPTION OF THE INVENTION

Figure 1:
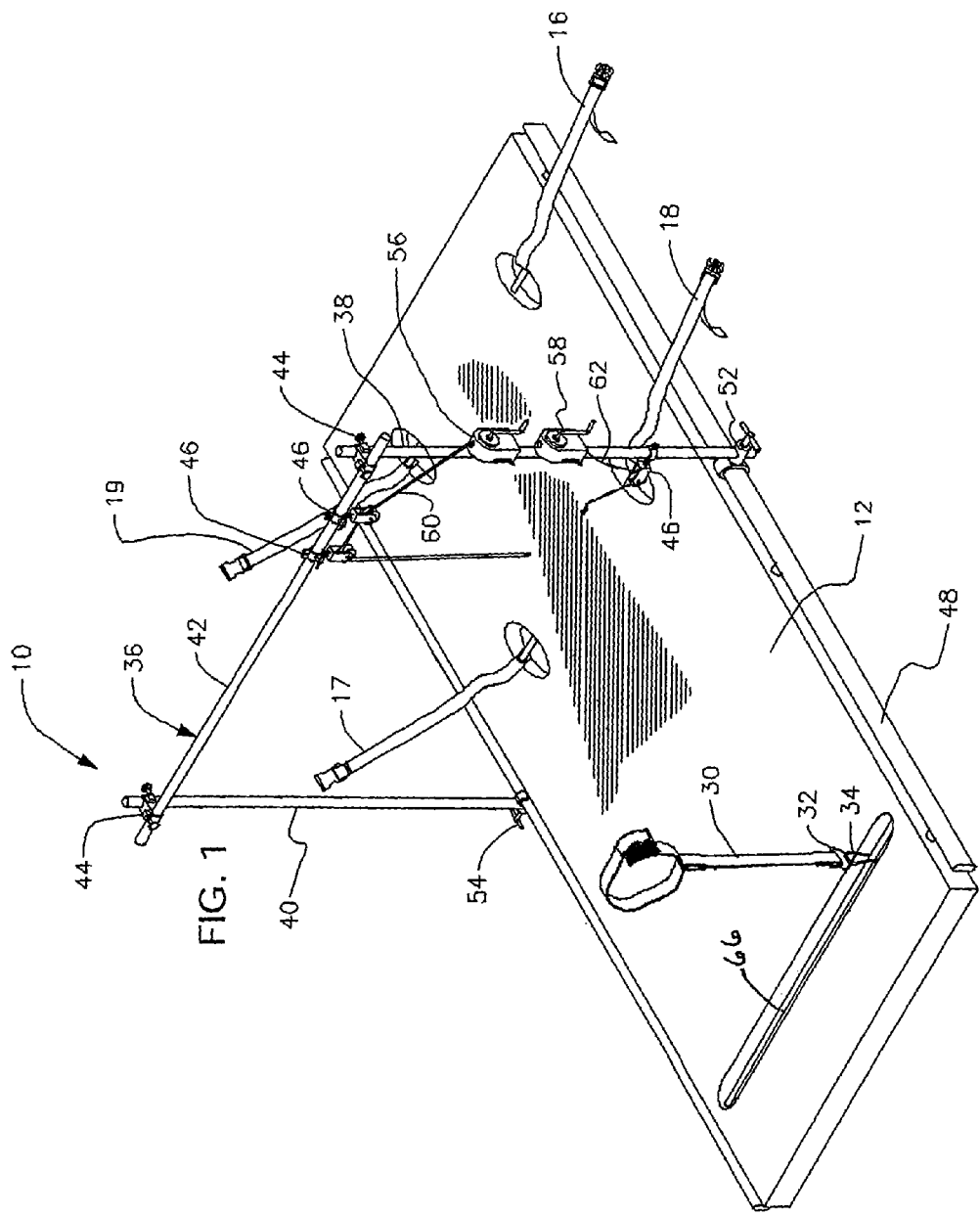
FIG. 1 is a perspective view of the passive hip reducer apparatus of this invention.

Throughout the following detailed description, the same reference numerals refer to the same elements in all figures.

Figure 2:
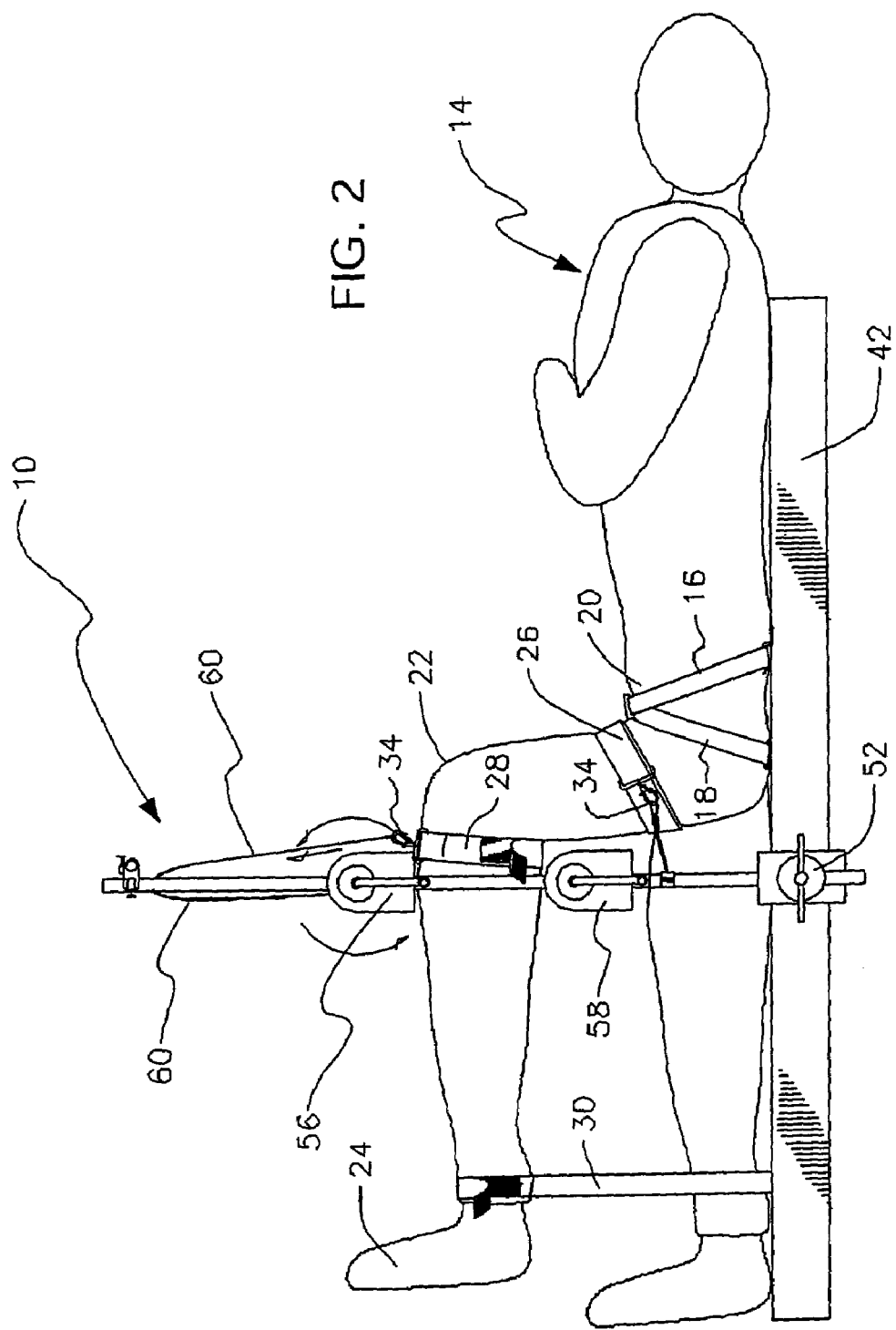
FIG. 2 is an elevational side view of a patient passively supported in the hip reducer apparatus with a leg sleeve.
Figure 3:
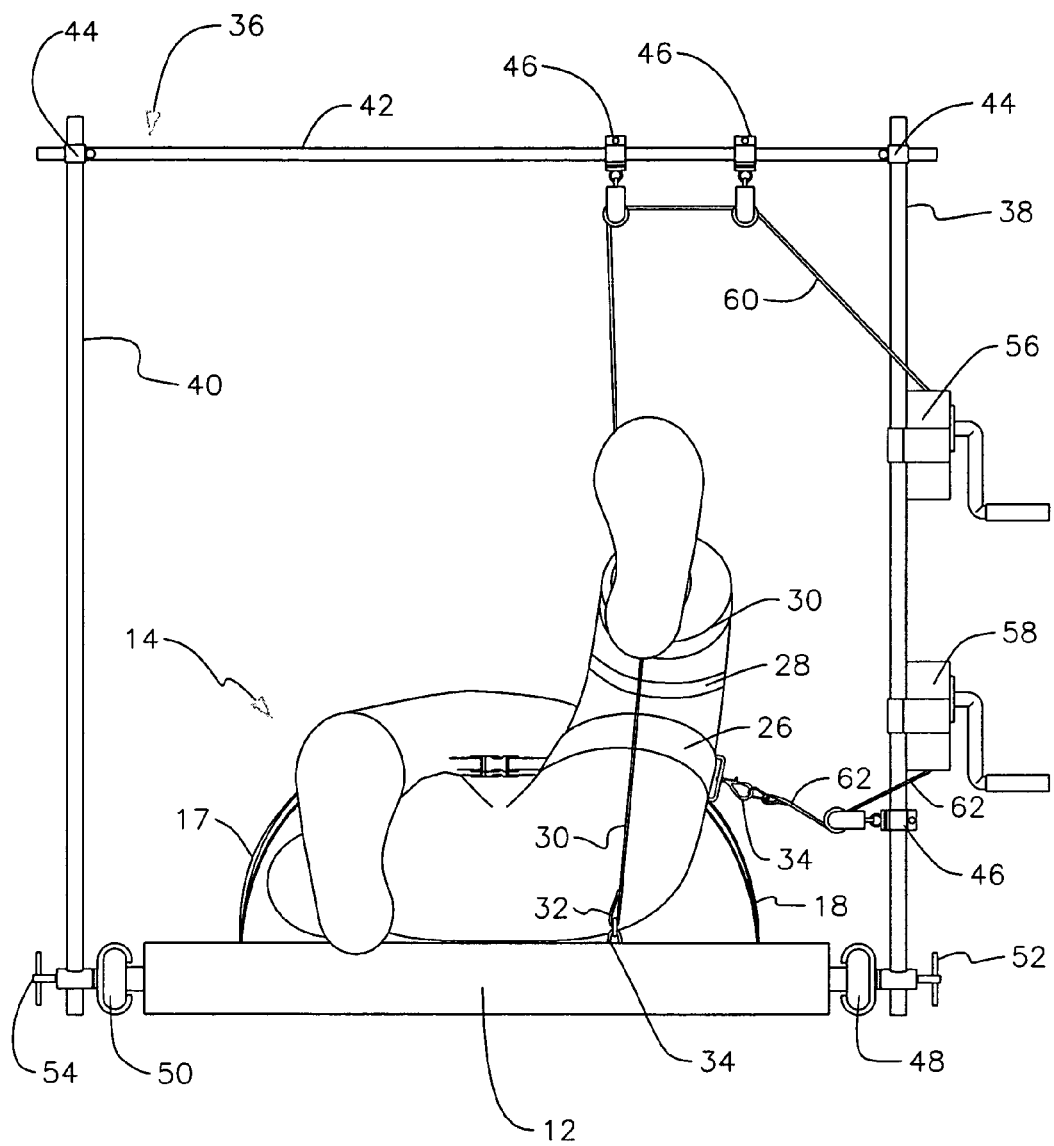
FIG. 3 is an elevational end view of the patient passively supported as in FIG. 2.

Referring to FIGS. 1–3, the passive hip reducer apparatus 10 has a substantially planar padded board 12 on which a patient 14 lies in a supine position. Two pair of pelvis straps 16 and 18 have ends that snap together around the midsection 20 of patient 14. Straps 17 snaps together crisscrossed with strap 16 and strap 19 snaps together crisscrossed with strap 18. A leg sleeve 22 is placed on the leg 24 of the patient 14 that is on the same side as the displaced hip. The leg sleeve 22 extends from the patient's ankle to the groin area. The leg sleeve 22 has upper hook and loop straps 26 near the groin area, middle hook and loop straps 28 just below the patient's knee and bottom hook and loop straps 30 just above the patient's ankle. A C-ring 32 fits around each strap and an identical cable fastening clip 34 is attached to each C-ring 32.

Figure 4:
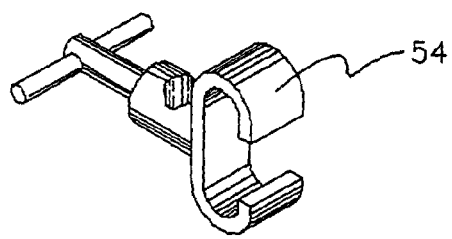
FIG. 4 is a perspective view of a left side table clamp employed to support the frame.
Figure 5:
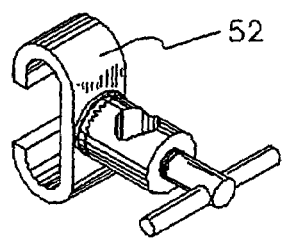
FIG. 5 is a perspective view of a right side table clamp employed to support the frame.
Figure 6:
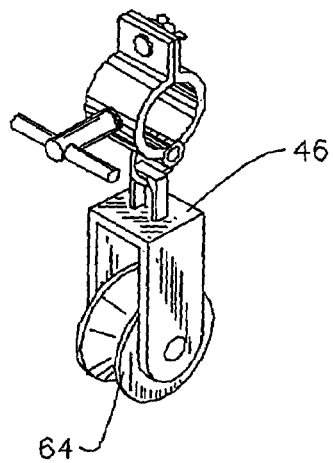
FIG. 6 is a perspective view of a clamp employed with a pulley.
Figure 7:
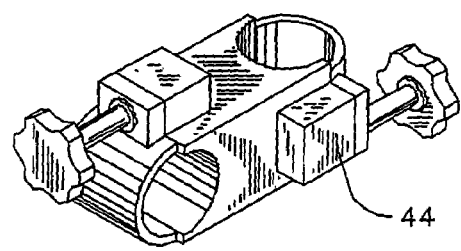
FIG. 7 is a perspective view of an upper frame clamp.

A frame 36 has two upright members 38 and 40 and a top horizontal member 42, all such members usually in the shape of a tube or bar, the top horizontal member 42 connecting with the tops of the upright members 38 and 40 using two clamps 44 seen more clearly in FIG. 7. The horizontal member 42 has a pair of clamp/pulleys 46 clamped in place. These clamp/pulleys 46 are seen more clearly in FIG. 6. The frame 36 moves horizontally on opposite side rails 48 and 50 attached to the longer sides of the padded board 12. The frame 36 is locked in place along the rails 48 and 50 with clamps 52 and 54 as seen respectively in FIGS. 5 and 4.

Depending on the side of the patient 14 which contains the dislocated hip winches 56 and 58 are mounted on an upright member 38 or 40. Assuming the dislocated hip is on the patient's left side as shown in FIGS. 2 and 3, the winches 56 and 58 are mounted on upright member 38. Winch 56 controls cable 60 which passes around rollers 64 in two pulleys 46 mounted on horizontal member 42. The cable 60 is connected to clip 34 on leg sleeve strap 28. Winch 56 is used to raise the patient's leg upright as shown in FIG. 2 so there is about a ninety degree angle between the patient's thigh and ankle. Ankle strap 30 prevents the ankle from raising up past the ninety degree angle. Winch 58 also mounted on upright member 38 controls a cable 62 passing around a pulley wheel 64 in pulley 46 mounted on upright member 38. Cable 62 is attached to the clip 34 on upper loop strap 26. Tension exerted on cable 62 pulls the patient's hip towards upright member 38.

The planar pad 12 is made from a firm urethane or like substance. The frame is preferably aluminum with the pulleys and clamps made of stainless steel.

The steps in treating a patient with a dislocated hip include first stretching the patient out on the pad 12 in a supine position and placing the leg sleeve 22 on the leg descending from the dislocated hip. Straps 26, 28 and 30 are differently colored over the groin, knee and ankle respectively. The straps are tightened. Clips 34 are attached to each of the c-clamps 32 on the leg sleeve straps. Thereafter, the two pulley clamps 46 are positioned on the affected side of the horizontal bar 42. The pelvis straps 16/17 and 18/19 are then fastened across the patient's pelvis and secured tightly in place. The cables are attached to the appropriate leg sleeve straps and then the knee winch 56 is turned either by hand or electrically to begin to raise the affected leg 24 to 90 degrees flexion. Consequently, the hip is flexed to 90 degrees flexion as well. The ankle strap 30 is fastened to the patient's ankle on the affected side and is adjusted to allow the patient's knee to stay at 90 degrees flexion. Thereafter the hip strap winch 58 is turned either by hand or electrically to apply tension to the hip joint. Eventually the patient will relax with the aid of medication previously given. The hip winch 58 is cranked again to create active outward traction on the upper leg at the groin strap 26. The practitioner moves the foot on the patient's affected leg 24 from side to side along track 66 until the hip is successfully reduced. No additional hand manipulation is required.

Equivalent elements and steps can be substituted for the elements and steps set forth above to create substantially the same function in substantially the same way and with substantially the same results.

Having thus described the invention, what is claimed and desired to be secured by Letters Patent is:

1. A passive hip reducer system for a patient having a dislocated hip, the system comprising:
    a substantially planar support pad supporting the patient in a supine position, a first end of at least one pelvis strap attached to an upper surface of the pad, and wrapped tightly around a waist of the patient;
    a leg sleeve around a leg of the patient from an ankle to a groin area on a same side as the dislocated hip;
    a first end of an ankle strap attached to the support pad and a second end to an ankle portion of the leg sleeve;
    a frame slidably attached to a rail on a first and second side of the support pad, the frame having a first and second upright structure attached at a bottom end to the rail on opposite sides of the support pad and a horizontal structure connecting a top end of the upright structures on each side of the support pad;
    a first winch attached to one of the upright structures, the winch controlling a cable attached via a pulley to a mid-section of the leg sleeve to raise the leg of the patient;
    a second winch attached to one of the upright structures, the winch controlling a cable attached via a pulley to an upper portion of the leg sleeve to pull the hip of the patient towards the first upright structure; and
    turning the first and second winch so that torque is exerted on the dislocated hip until such time as the dislocated hip returns to a normal position in the patient.

2. The passive hip reducer system according to claim 1, wherein the support pad is rectangular in shape.

3. The passive hip reducer system according to claim 1, wherein there are two pair of pelvis straps, each pair engaged together in a crisscrossed pattern around the waist of the patient.

4. The passive hip reducer system according to claim 1, wherein hook and loop straps are employed around an upper, middle and lower portion of the leg sleeve.

5. The passive hip reducer system according to claim 4, wherein a C-ring engages the hook and loop straps around the upper, middle and lower portion of the leg sleeve.

6. The passive hip reducer system according to claim 5, wherein a clip is attached to each C-ring.

7. The passive hip reducer system according to claim 1, wherein the first and second upright and horizontal structures are cylindrical tubes.

8. The passive hip reducer system according to claim 1, wherein the fist and second upright and horizontal structures are solid rods.

9. The passive hip reducer system according to claim 1, wherein a clamp fixedly connects the upright structures of the frame to the rails when the frame is positioned over a knee of the patient.

10. The passive hip reducer system according to claim 1, wherein the first and second winch is attached to the upright structures nearest the dislocated hip of the patient.

11. The passive hip reducer system according to claim 1, wherein two pulleys are clamped to the horizontal frame structure to support the cable controlled by the first winch.

12. A method of reducing a dislocated hip in a patient, the method comprising:
    (a) laying the patient on a substantially planar support pad;
    (b) tightly attaching straps around a waist of the patient, the straps having at least one end attached to the support pad;
    (c) wrapping a leg of the patient descending from the dislocated hip in a leg sleeve covering the leg from an ankle to a groin area of the patient;
    (d) clamping a frame having two upright members and a top horizontal member to rails positioned on opposite sides of the pad on each side of the patient;
    (e) mounting a first winch on an upright member adjacent the leg containing the leg sleeve, the first winch controlling a cable passing through pulleys suspended from the horizontal frame member, the cable attached at a distal end from the first winch to a portion of the leg sleeve just below the knee of the patient;
    (f) turning the first winch to lift the patient's leg;
    (g) attaching an ankle strap to the pad at one end and to the leg sleeve just above the patient's ankle so that the leg of the patient is lifted to a position wherein the leg below the knee is at about a ninety degree angle to a thigh of the patient;
    (h) mounting a second winch on the upright member containing the first winch, the second winch controlling a cable passing through a pulley clamped to the same upright member, the cable attached at a distal end from the second winch to a portion of the leg sleeve adjacent the patient's groin area;
    (i) turning the second winch to pull the patient's hip towards the upright member mounting the winches; and
    (j) maintaining tension on the leg sleeve until the patient's dislocated hip returns to a normal position in a hip socket.

13. The method of reducing a dislocated hip according to claim 12, wherein hook and loop straps are wrapped around a portion of the leg sleeve adjacent the groin area, adjacent an area below the knee and an area adjacent the ankle.

14. The method of reducing a dislocated hip according to claim 13, wherein a C-ring and clip is connected to each hook and loop strap.

15. The method of reducing a dislocated hip according to claim 14, wherein the distal end of the cable controlled by the first winch is attached to the clip connected to the hook and loop strap adjacent an area below the knee and distal end of the cable controlled by the second winch is attached to the clip connected to the hook and loop strap adjacent the groin area.

16. An apparatus for passively returning a dislocated hip of a patient to its normal socket position, the apparatus comprising:

a substantially planar support pad adapted to support the patient in a supine position;

pairs of straps adapted to be crisscrossed around a waist of the patient, the straps anchored in the pad;

a leg sleeve adapted to be wrapped around a leg of a patient descending from the dislocated hip, the leg sleeve adapted to cover the leg from an ankle to a groin area;

an ankle strap anchored to the pad at one end and adapted to be attached at a second end to an ankle area of the leg sleeve;

a frame having two upright members connected at a top portion to a horizontal member, the upright members attached at opposite sides of the pad to a rail parallel to and attached to a longer side of the pad, the frame attached to the rails approximately over the groin area of the patient;

a first winch attached to the upright member adjacent the leg sleeve the first winch controlling a cable passing through pulleys descending from the horizontal frame member, a cable end connected to a portion of the leg sleeve just below the patient's knee; and a second winch attached to the upright member adjacent the leg sleeve, the second winch controlling a cable passing through a pulley attached to the upright member adjacent the leg sleeve, a cable end connected to a portion of the leg sleeve adjacent the groin area, so that when a patient with a dislocated hip is placed in the apparatus, tension on the leg sleeve exerted by the first and second winch will cause the dislocated hip to return to a hip socket.

* * * * *